United States Patent [19]
Sata et al.

[11] Patent Number: 6,008,177
[45] Date of Patent: Dec. 28, 1999

[54] GERMICIDAL COMPOSITION

[75] Inventors: Juri Sata; Yoshinori Tamura; Keiko Hasebe; Tadashi Moriyama, all of Wakayama, Japan

[73] Assignee: Kao Corporation, Tokyo, Japan

[21] Appl. No.: 09/077,875

[22] PCT Filed: Nov. 26, 1996

[86] PCT No.: PCT/JP96/03451

§ 371 Date: Jun. 5, 1998

§ 102(e) Date: Jun. 8, 1998

[87] PCT Pub. No.: WO97/21348

PCT Pub. Date: Jun. 19, 1997

[30] Foreign Application Priority Data

Dec. 8, 1995 [JP] Japan ..................... 7-320460

[51] Int. Cl.$^6$ ............... C11D 7/32; C11D 7/36; C11D 1/62

[52] U.S. Cl. .......... 510/391; 510/119; 510/131; 510/467; 510/504

[58] Field of Search .............. 510/119, 131, 510/382, 391, 467, 504

[56] References Cited

U.S. PATENT DOCUMENTS

| | | | |
|---|---|---|---|
| 4,036,950 | 7/1977 | Baines et al. | 424/54 |
| 4,748,158 | 5/1988 | Biermann et al. | 514/25 |
| 4,920,100 | 4/1990 | Lehmann et al. | 514/23 |

FOREIGN PATENT DOCUMENTS

| | | |
|---|---|---|
| 018492 A1 | 3/1980 | European Pat. Off. . |
| 537426 A1 | 4/1993 | European Pat. Off. . |
| 2335901 | 7/1973 | Germany . |
| 05-85905 | 4/1993 | Japan . |
| 05-221805 | 8/1993 | Japan . |
| 95/01414 | 1/1995 | WIPO . |

Primary Examiner—Yogendra Gupta
Assistant Examiner—John R. Hardee
Attorney, Agent, or Firm—Oblon, Spivak, McClelland, Maier & Neustadt, P.C.

[57] ABSTRACT

A germicidal composition comprising:

i) a compound of formula (1):

$$\left[ \begin{array}{c} R^1 \\ R^2 \end{array} \!\!\!\! \begin{array}{c} R^3 \\ \overset{\oplus}{N} \\ R^4 \end{array} \right] \;\; {}^{\ominus}\text{O}-\overset{\overset{\displaystyle O}{\|}}{\underset{\underset{\displaystyle OM}{|}}{P}}-OR^5 \quad (1)$$

wherein at least one of $R^1$, $R^2$ and $R^3$ represents a linear or branched $C_{8-30}$ alkyl or alkenyl group and the remaining groups are the same or different and individually represent a methyl, ethyl or benzyl group; $R^4$ represents a methyl or ethyl group; $R^5$ represents a linear or branched $C_{1-30}$ alkyl or alkenyl group, or a polyoxyalkylene alkyl ether or polyoxyalkylene alkenyl ether having a linear or branched $C_{1-30}$ alkyl or alkenyl group; and M represents a hydrogen atom or an alkali metal atom; and ii) a compound of formula (2):

$$\left[ \begin{array}{c} R^1 \\ R^2 \end{array} \!\!\!\! \begin{array}{c} R^3 \\ \overset{\oplus}{N} \\ R^4 \end{array} \right] \;\; {}^{\ominus}\text{O}-\overset{\overset{\displaystyle O}{\|}}{\underset{\underset{\displaystyle OR^7}{|}}{P}}-OR^6 \quad (2)$$

wherein $R^1$ to $R^4$ have the same meanings as defined above and $R^6$ and $R^7$ are the same or different and individually have the same meanings as $R^5$, wherein the weight ratio of compound (1) to compound (2) is from 99:1 to 80:20.

22 Claims, No Drawings

GERMICIDAL COMPOSITION

TECHNICAL FIELD

The present invention relates to germicidal compositions, preferably, germicidal compositions for the body. The germicidal compositions for the body produce low levels of skin irritation and have excellent sterilizing properties and can be used in the disinfection and sterilization of hands and fingers; the disinfection and sterilization of human skin, such as, for example, facial skin and the human scalp, and hair, such as, for example, hair of the head; and the disinfection and sterilization of animal skin.

BACKGROUND ART

Quaternary ammonium salts have excellent sterilizing power. They have been used for a variety of conventional purposes, including the sterilization and disinfection of buildings and environments, such as, for example, barns and food plants, and the antisepsis of wood. They have also been used for the sterilization of hands and fingers and for the sterilization of skin upon surgical operation.

Unfortunately, however, quaternary ammonium salts have a tendency to be highly irritable to the skin and have a tendency to cause hand chapping or eruption when used ordinarily. As a result, containing quaternary ammonium salts are limited in their concentration and range for ordinary everyday use. Therefore, they have not produced sufficiently effective results when used for the skin or the like.

With the intent of coping with such problems, a disinfectant antiseptic wherein the counter anion of a quaternary ammonium salt is variably changed and which produces reduced skin irritation is disclosed in Japanese Patent Laid-Open No. 218605/1990.

However, these quaternary ammonium salts are not uniform in their effects, and consequently, stable effects cannot be obtained.

Therefore, there exists a demand for a germicide, preferably a germicide for the body, which produces reduced or little skin irritation, and has greater safety and excellent sterilizing power.

DISCLOSURE OF THE INVENTION

Accordingly, after extensive research, one object of the present invention is a germicidal composition, preferably a germicidal composition for the body, which produces very low levels of skin irritation and exhibits excellent sterilizing power.

Another object of the invention is a germicidal composition, preferably a germicidal composition for the body, comprising by mixing, in a specific proportion, two quaternary ammonium salt compounds, each of which comprises a specific counter ion, which produces remarkably little skin irritation and has excellent sterilizing power.

Another object of the present invention is a germicidal composition, preferably a germicidal composition for the body, which produces little skin irritation, excellent sterilizing power and detergency.

Another object of the present invention is a germicidal detergent composition, preferably a germicidal detergent composition for the body, comprising a composition comprising quaternary ammonium salt(s) in combination with a surfactant such as, for example, an alkyl glycoside or sugar amide.

Still another object of the present invention is a germicidal composition, preferably a germicidal composition for the body, producing even less skin irritation than the above mentioned compositions, comprising a quaternary ammonium salt(s) and a humectant such as, for example, sorbitol or glycerin.

Another object of the present invention is a method for washing, preferably the skin or hair, comprising applying a germicidal or germicidal detergent composition of the present invention.

Another object of the present invention is a method for sterilizing, preferably the skin, comprising washing the skin with a germicidal or germicidal detergent composition of the present invention.

These and other objects of the present invention are made possible by germicidal compositions, preferably for the body, which exhibit excellent sterilizing power and detergency and little skin irritation. The present germicidal compositions are ideal for use on the skin or hair of human bodies such as fingers, hands, facial skin, hair of the head or scalp, and also for use on the skin of animals.

DETAILED DESCRIPTION OF THE PREFERRED EMBODIMENTS

The germicidal composition, preferably the body, of the present invention comprises i) a quaternary ammonium compound of formula (1):

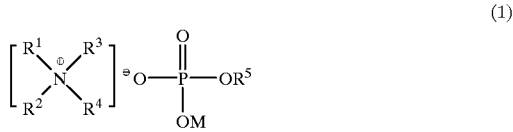

(1)

wherein at least one of $R^1$, $R^2$ and $R^3$ represents a linear or branched $C_{8-30}$ alkyl or alkenyl group and the remaining groups are the same or different and individually represent a methyl, ethyl or benzyl group;

$R^4$ represents a methyl or ethyl group;

$R^5$ represents a linear or branched $C_{1-30}$ alkyl or alkenyl group, or a polyoxyalkylene alkyl ether or polyoxyalkylene alkenyl ether having a linear or branched $C_{1-30}$ alkyl or alkenyl group; and M represents a hydrogen atom or an alkali metal atom; and ii) a quaternary ammonium compound of formula (2):

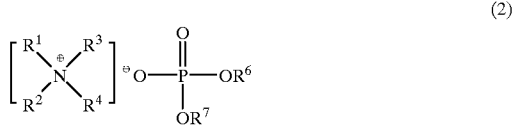

(2)

wherein $R^1$ to $R^4$ have the same meanings as defined above; and $R^6$ and $R^7$ are the same or different and individually have the same meaning as $R^5$ as defined above; and wherein the weight ratio of quaternary ammonium salt compound (1) to quaternary ammonium salt compound (2) is of 99:1 to 80:20.

The germicidal detergent composition, preferably for the body, of the present invention comprises the following components (a) and (b):

(a) a composition comprising the quaternary-ammonium-salts of formulas (1) and (2); and (b) one or more surfactants selected from the group consisting of alkyl glycosides and sugar amides.

Another germicidal detergent composition, preferably for body, of the present invention comprises the following components (a) and (c):

(a) a composition comprising the quaternary-ammonium-salts of formulas (1) and (2); and (c) at least one of a humectant selected from the group consisting of sorbitol, glycerin and a mixture thereof.

The method of washing, preferably, the skin or hair, of the present invention comprises applying one of the above-described germicidal and/or germicidal detergent compositions.

The method of sterilizing, preferably the skin, of the present invention comprises washing the skin with one of the above-described germicidal and/or germicidal detergent compositions.

The quaternary ammonium compounds of formulas (1) and (2) of the present invention, examples of the linear $C_{8-30}$ alkyl group represented by $R^1$, $R^2$ or $R^3$ include, but are not limited to, n-octyl, n-nonyl, n-decyl, n-undecyl, n-dodecyl, n-tetradecyl, n-hexadecyl and n-octadecyl; examples of the branched $C_{8-30}$ alkyl group represented by $R^1$, $R^2$ or $R^3$ include, but are not limited to, 2-ethylhexyl, 2-methyldodecyl, 2-methyltetradecyl, 2-butyloctyl, 2-hexyldecyl, 2-heptylundecyl, 2-octyldodecyl and 2-decyltetradecyl; and examples of the linear or branched $C_{8-30}$ alkenyl group represented by $R^1$, $R^2$ or $R^3$ include, but are not limited to, hexadecenyl, octadecenyl, hexadecadienyl, octadecadienyl and eicosadienyl groups.

Each of the compounds represented by the formulas (1) and (2) may be derived from a synthetic product or natural product.

The germicidal and/or germicidal detergent compositions may comprise a mixture of at least two quaternary ammonium compounds selected from the group of quaternary ammonium compounds containing the above-exemplified groups as $R^1$, $R^2$ and $R^3$.

Preferably, the quaternary ammonium compounds of formulas (1) and (2), are compounds wherein $R^1$ is a linear or branched $C_{8-30}$ alkyl or alkenyl group, $R^2$ is a benzyl group and $R^3$ is a methyl group. Of these quaternary ammonium compounds, compounds wherein $R^1$ is a linear $C_{8-20}$ alkyl group is particularly preferred.

For the quaternary ammonium compounds of formulas (1) and (2) of the present invention, examples of the linear $C_{1-30}$ alkyl group represented by $R^5$, $R^6$ or $R^7$, include, but are not limited to, methyl, ethyl, n-propyl, n-butyl, n-pentyl, n-hexyl and n-heptyl groups, and the linear alkyl groups exemplified above as $R^1$, $R^2$ and $R^3$; examples of the branched $C_{1-30}$ alkyl group include, but are not limited to, isopropyl, isobutyl, sec-butyl and tert-butyl groups, and the branched alkyl groups exemplified above as the $R^1$, $R^2$ and $R^3$; and examples of the alkenyl group include allyl and methallyl groups and the alkenyl groups exemplified above as $R^2$ and $R^3$.

Illustrative examples of the polyoxyalkylene alkyl ether containing a linear or branched $C_{1-30}$ alkyl group represented by $R^5$, $R^6$ or $R^7$, include, but are not limited to, polyoxyethylene cetyl ether, polyoxyethylene stearyl ether, polyoxyethylene hexadecyl ether and polyoxypropylene cetyl ether.

Illustrative of the polyoxyalkylene alkenyl ether containing a linear or branched $C_{1-30}$ alkenyl group represented by $R^5$, $R^6$ or $R^7$, include, but are not limited to, polyoxyethylene hexadecenyl ether and polyoxyethylene octadecenyl ether. Here, the number of moles of the oxyalkylene group added is preferably 1–30.

Preferably, $R^5$, $R^6$ and $R^7$ represent linear or branched $C_{12-20}$ alkyl or alkenyl groups. More preferably, $R^5$, $R^6$ and $R^7$ represent linear $C_{12-20}$ alkyl groups.

Examples of the alkali metal represented by M in formula (1) include potassium and sodium. Preferably, M is a hydrogen atom.

Preferably, the quaternary ammonium compounds of formula (1) or (2) of the present invention are those containing a linear or branched $C_{8-20}$ alkyl or alkenyl group as $R^1$, a benzyl group as $R^2$, a methyl group as $R^3$, linear or branched $C_{12-20}$ alkyl groups as $R^5$, $R^6$ and $R^7$, respectively, and a hydrogen atom as M.

The quaternary ammonium salt represented by the formulas (1) or (2) of the present invention, can be prepared in a manner known to date, for example, by converting a quaternary ammonium salt whose counter ion is a halogen atom into an OH-type quaternary ammonium salt using an ion exchange resin, and then neutralizing with a phosphate ester compound corresponding to an anionic residue. In this case, it is possible that the quaternary ammonium salt so obtained contains an alkali metal salt, amine salt, organic amine salt or the like to such an extent that the function of the present invention is not impaired.

Alternatively, it is possible to prepare the quaternary ammonium salt by treating a quaternary ammonium halide under alkaline conditions, desalting by electrodialysis and then neutralizing with a phosphate ester compound corresponding to an anionic residue.

Preferably, the quaternary ammonium salt represented by formula (1) or (2) of the present invention is prepared by the process of mixing, in a mixed solvent of an organic solvent and water, a quaternary ammonium salt whose counter ion is a halogen atom with a phosphate ester compound (containing an alkali metal as M) corresponding to an anionic residue; heating for reaction the resulting mixture; subjecting the reaction mixture to phase separation; and then obtaining the target compound from the organic phase. In this preparation process, the preferred examples of the organic solvent include ethanol and isopropanol. It is also preferred to mix the quaternary ammonium salt whose counter ion is a halogen atom with a phosphate ester compound corresponding to an anionic residue at a molar ratio of preferably, 1.5:1 to 1:1.5, more preferably of 1.2:1 to 1:1.2. Water and the organic solvent are mixed at a weight ratio of, preferably, from 10:1 to 1:2, more preferably, from 6:1 to 1:1. In addition, water is added to the quaternary ammonium halide at a weight ratio of, preferably, from 20:1 to 2:1, more preferably, from 12:1 to 5:1.

Upon preparation of the quaternary ammonium compounds represented by formula (1) or (2), chloride ions derived from the raw materials or reaction by-products exist in the target compound. The term "chloride ion content" as used herein is defined as a value obtained by subjecting the chloride ions contained in a sample to potentiometric titration with a silver nitrate solution, determining the amount of the chloride ions from the consumption amount of the solution and then expressing the amount in terms of percentage (%) relative to the sample. The chloride ion content in the quaternary ammonium compound represented by formula (1) or (2) is preferably less than or equal to 2.0%, more preferably less than or equal to 1.0%, and most preferably, less than or equal to 0.6%. A chloride ion content exceeding 2.0% increases skin irritation and corrodes a container used for the preparation or treatment of the quaternary ammonium compound and thus chloride ion content of greater than 2% and should be avoided.

In order to lessen skin irritation and to obtain excellent sterilizing power, the germicidal composition, preferably for the body, according to the present invention should comprise a mixture of quaternary ammonium compounds of formulas (1) and (2) at a weight ratio of, preferably, from 99:1 to 80:20, more preferably, from 98:2 to 83:17.

No particular limitation is imposed on the amounts of the quaternary ammonium compounds of formulas (1) and (2) in the germicidal composition of the present invention. However, it is desired to mix them at a total concentration falling within a range of, preferably, from 0.005 to 90 wt. %, more preferably, from 0.01 to 50 wt. %, and even more preferably, from 0.02 to 25% based on the whole composition.

The germicidal detergent composition, preferably for the body, which produces little skin irritation, excellent sterilizing properties and good detergency of the present invention comprises (b) one or more surfactants selected from the group consisting of alkyl glycosides and sugar amides in combination with (a) a composition comprising the quaternary ammonium compounds of the formulas (1) and (2) of the present invention.

Examples of alkyl glycosides which can be used for such a germicidal detergent composition include compounds represented by the following formula (3):

wherein $R^8$ represents a linear or branched $C_{1-18}$ alkyl, alkenyl or alkylphenyl group;

$R^9$ represents a $C_{2-4}$ alkylene group;

G represents a $C_{5-6}$ reducing sugar;

m is an integer from 0–10; and n is an integer from 1–10 on average.

In the above formula, preferably, $R^8$ represents a linear or branched $C_{8-16}$ alkyl group (decyl, lauryl, myristyl or the like). Preferably, m stands for 0–10, more preferably for 0–3, and most preferably for 0. Furthermore, the glycoside portion is a hydrophilic group (corresponding to G in formula (3)) having $C_{5-6}$ reducing sugar as a fundamental unit. Examples of the reducing sugar include glucose, galactose and fructose. The polymerization degree, S, (corresponding to n in formula (3)) of the glycoside is 1–10 of which at least 80% has a polymerization degree of 1–4. The average polymerization degree, S, can be measured by a proton NMR method.

Examples of the alkyl glycoside surfactant include, but are not limited to, β-alkyl saccharides such as octyl glucoside, nonyl glucoside, decyl maltoside, dodecyl maltoside, tridecyl maltoside and polyoxyethylene (2E.O.) dodecyl glucoside, each being synthesized by the Koenigs-Knorr method known to date; reducing sugars such as glucose, galactose and maltose; and those synthesized from higher alcohols or polyoxyethylene alkyl ether alcohols (U.S. Pat. Nos. 3,219,656, 3,839,318 and 4,223,129).

Of these, alkyl glycosides of the formula (3) wherein $R^8$ represents a linear or branched $C_{9-16}$ alkyl group, G represents a glucose, n stands for 1.1–4 on average and m stands for 0 are particularly preferred.

The term "sugar amide" as used herein means a compound represented by the following formula (4):

wherein $R^{10}$ represents a linear or branched $C_{5-31}$ alkyl or alkenyl group which may be substituted by a hydroxyl group; $R^{11}$ represents a hydrogen atom or a linear or branched $C_{1-4}$ alkyl group which may be substituted by a hydroxyl group; and Z represents a sugar residue or a sugar alcohol residue or an alkoxylated derivative of the residue.

In the formula (4), preferred examples of $R^{10}$ include $C_{7-19}$ alkyl and alkenyl groups, with $C_{11-17}$ alkyl and alkenyl groups being particularly preferred. Preferred examples of $R^{11}$ include linear $C_{1-4}$ alkyl groups, with methyl and ethyl groups being particularly preferred. Among the residues and derivatives represented by Z, preferred examples of the reducing sugar include reducing sugar residues. Examples of preferred reducing sugars include glucose, fructose, maltose, lactose, galactose, mannose and xylose. Examples of the sugar alcohol are those derived from a reducing sugar by reductive amination reaction and include, but are not limited to, $-CH_2(CHOH)_{1}-CH_2OH$ and $-CH(CH_2OH)-(CHOH)_{1-1}-CH_2-OH$ (in which 1 stands for an integer between 3–5, preferably, 4).

In the germicidal detergent composition, preferably for the body, according to the present invention, no particular limitation is imposed on the amount of component (a). However, it is desired to add the quaternary ammonium compounds of formulas (1) and (2) in total percentages by weight of composition, preferably, 0.005–90 wt. %, more preferably, of 0.01 to 50 wt. %, and even more preferably, 0.02–25 wt. %. The surfactant or component (b) is added preferably in an amount of 3–30 wt. % of the total composition, preferably, 5–20 wt. %.

Preferably, the composition is used either without dilution or after dilution with water.

The degree of skin irritation produced by the above-described germicidal composition or germicidal detergent composition according to the present invention is lessened when the composition further comprises sorbitol and/or glycerin. The amount of sorbitol and/or glycerin is preferably 1–30 wt. %, more preferably, 3–20 wt. %, based on the entire weight of the composition.

The germicidal or germicidal detergent composition of the present invention can further comprise a salt, a surfactant other than those already mentioned, and a water-soluble thickener as needed to the extent that the effects of the compositions of the present invention are not impaired.

Examples of the salt include, but are not limited to, metal salts of a carboxylic acid such as succinic acid, malonic acid, citric acid, gluconic acid and glutaric acid; metal salts of a phosphoric acid compound such as tripolyphophoric acid, hexamethaphosphoric acid and phosphoric acid; and inorganic salts such as $Na_2SO_4$ and $MgSO_4$. They may be used either singly or in combination.

Examples of additional surfactants include nonionic, anionic and amphoteric surfactants. They can be added in an amount of 0–30 wt. %, preferably 0–20 wt. %, more preferably 2–5 wt. %, based on the total germicidal composition, preferably for the body.

Examples of the anionic surfactant include, but are not limited to, higher fatty acid salts, alkylsulfates, alkyl sulfonates, polyoxyethylene alkylsulfates, alkylbenzene sulfonates, N-acylsarcosine salts, N-acyl-N-methyltaurine salts, alfa-olefin sulfonates, alkyl ether acetates, polyoxyethylene alkyl ether acetates and polyoxyethylene alkylamide ether acetates.

Examples of the nonionic surfactant include, but are not limited to, sucrose fatty acid esters, polyglycerin fatty acid esters, polyoxyalkylene alkyl ethers, alkylamine oxides and fatty acid polyhydric alcohol esters.

Examples of the amphoteric surfactants include, but are not limited to, amidoamino acid base, carbobetaine base, sulfobetaine base, amidesulfobetaine base, imidazolinium betaine base, amino acid betaine base and phosphobetaine base.

The water-soluble thickener can be any of those selected from the group of natural, semi-synthetic and synthetic water-soluble thickeners. Such a water-soluble thickener is added in an amount of about 0–3.0 wt. %, preferably about 0.05–1.5 wt. %, more preferably 0.05–0.5 wt. %, based on the whole composition.

Examples of natural water-soluble thickeners include, but are not limited to, bacteria derived xanthan gum and xanflow and plant-derived pectin, gum arabic and guar gum.

Examples of semi-synthetic water-soluble thickeners include, but are not limited to, cellulose and starch derivatives which have been methylated, carboxyalkylated or hydroxyalkylated, such as methyl cellulose, carboxymethyl cellulose and hydroxymethyl cellulose.

Examples of synthetic water-soluble thickeners include, but are not limited to, polyacrylate salts, polymaleate salts, polyvinyl pyrrolidone and pentaerythritol EO adducts.

In addition, it is preferred to prepare the composition of the present invention as an ethanol germicidal composition containing ethanol as a base. No particular limitation is imposed on the amount of ethanol to be added as a base. However, it is preferably to add the ethanol in an amount of 20–90 wt. %, more preferably 25–85 wt. %, based on the whole composition.

The body germicidal composition according to the present invention can be used for human bodies or animal bodies. For example, it can be prepared in the form of a pharmaceutical disinfectant antiseptic, a medical disinfectant antiseptic for animals, a cosmetic, a shampoo, a soap, a rinse or a detergent.

Pharmaceutical disinfectant antiseptics include, for example, disinfectant antiseptics that can be used by immersing fingers and hands in a diluted solution thereof and scrubbing type sterilizing detergents that can be used by scrubbing hands.

Medical disinfectant antiseptics for animals include, for example, disinfectant antiseptics for animal skin.

Examples of a cosmetic include germicidal cream, germicidal lotion, and germicidal care products.

Examples of a shampoo, a soap, a rinse or a detergent include medicated shampoo, medicated soap, hand wash having sterilizing property, medicated rinse, deodorant and sanitizer.

Of these various applications, a germicidal detergent for skin and hair is particularly preferred.

EXAMPLES

The present invention will hereafter be described in further detail by examples. It should however be borne in mind that the present invention is not limited to or by the following examples.

Example 1

Examples of quaternary ammonium salts of the present invention and Comparative Examples of quaternary ammonium salts used in the following tests are summarized in Table 1. The chloride ion content of the quaternary ammonium salts shown in Table 1 is less than or equal to 1.0%.

TABLE 1

|  |  | Cation portion | Counter ion portion[1] MAP-DAP[2] |
|---|---|---|---|
| Invention Products | Quaternary ammonium salt 1 | $CH_3(CH_2)_{11}-\overset{\oplus}{N}(CH_3)(CH_2Ph)-CH_3$ | $O^{\ominus}-\underset{O}{\overset{OR}{\underset{\|}{P}}}-O-(CH_2)_{15}CH_3$ | 95:5 |
|  | Quaternary ammonium salt 2 | $CH_3(CH_2)_{11}-\overset{\oplus}{N}(CH_3)(CH_2Ph)-CH_3$ | $O^{\ominus}-\underset{O}{\overset{OR}{\underset{\|}{P}}}-O-(CH_2)_{15}CH_3$ | 85:15 |

TABLE 1-continued

| | | Cation portion | Counter ion portion[1] | |
| --- | --- | --- | --- | --- |
| | | | | MAP-DAP[2] |
| Comparative Products | Quaternary ammonium salt 3 | CH₃(CH₂)₁₁—N⁺(CH₃)(CH₃)(CH₂C₆H₅) | O⁻—P(=O)(OR)—O—(CH₂)₁₅CH₃ | 100:0 |
| | Quaternary ammonium salt 4 | CH₃(CH₂)₁₁—N⁺(CH₃)(CH₃)(CH₂C₆H₅) | O⁻—P(=O)(OR)—O—(CH₂)₁₅CH₃ | 70:30 |
| | Quaternary ammonium salt 5 | CH₃(CH₂)₁₁—N⁺(CH₃)(CH₃)(CH₂C₆H₅) | O⁻—P(=O)(OR)—O—(CH₂)₁₅CH₃ | 50:50 |

[1]: R represents a hydrogen atom or $C_{14}H_{13}$.
[2]: MAP represents a monoalkyl phosphate, while DAP represents dialkyl phosphate. The number stands for weight ratio contained in the counter ion portion.

Sterilizing activity of a quaternary ammonium salt

The sterilizing activity of the quaternary ammonium salts of the present invention against various microorganisms was studied. The sterilizing activity was determined from the minimum sterilizing concentration ($\mu$g/ml, 24 h). The results are summarized in Table 2.

TABLE 2

| | Escherichia coli | Staphylococcus aureus | Candida albicans | Aspergillus niger |
| --- | --- | --- | --- | --- |
| Quaternary ammonium salt 1 | 10 | 5 | 10 | 200 |
| Quaternary ammonium salt 2 | 10 | 5 | 10 | 200 |
| Quaternary ammonium salt 3 | 10 | 5 | 20 | 200 |
| Quaternary ammonium salt 4 | 200 | 250 | 200 | 1000< |
| Quaternary ammonium salt 5 | 400 | 500 | 400 | 1000< |

Antimicrobial activity of a quaternary ammonium salt

The antimicrobial activity of the quaternary ammonium salts listed in Table 1 against bacteria was studied. The antimicrobial test was conducted as follows: the bacteria to be tested (Staphylococcus aureus; IF012732) was pre-incubated on an SCD medium (product of Nippon Seiyaku Co., Ltd.) at 35° C. The pre-incubated culture was smeared onto an SCD agar medium (product of Nippon Seiyaku Co., Ltd.). A paper disk (thick, product of ADVANTEC Co.) having a diameter of 8 mm, on which 50 $\mu$l of a 0.5% aqueous solution of a quaternary ammonium salt was poured and which was then washed with water, was placed on the agar medium onto which the culture had been smeared. Twenty four hours later at 35° C., the diameter (mm) of an inhibition zone was measured, whereby antibacterial activity was judged. Results are shown in Table 3.

TABLE 3

|  | *Staphylococcus aureus* |
| --- | --- |
| Quaternary ammonium salt 1 | 46 (mm) |
| Quaternary ammonium salt 2 | 44 |
| Quaternary ammonium salt 3 | 18 |
| Quaternary ammonium salt 4 | 15 |
| Quaternary ammonium salt 5 | 10 |

Skin irritation (I) of a quaternary ammonium salt

A side abdominal part of a Hartley white guinea pig (female) having a body weight of 300–400 g was depilated by an electric hair clipper or electric razor. Three to six hours later, a circle of about 2 cm in diameter was drawn by the tip of a Teflon rod which had been dipped in a sample of a 2.5% aqueous solution of a quaternary ammonium salt, whereby the sample was applied to the depilated part. The coating was conducted once a day for four days. The condition of the part of the skin coated with the sample was judged prior to each coating. The judgement was conducted four times. The skin where no reaction was recognized and the skin where erythema was recognized were distinguished. The number of the guinea pigs in one group (consisting of 5 guinea pigs) which were recognized to have erythema is shown in Table 4.

TABLE 4

|  | Average Grade | | | |
| --- | --- | --- | --- | --- |
|  | First | Second | Third | Fourth |
| Quaternary ammonium salt 1 | 0 | 0 | 0 | 2 |
| Quaternary ammonium salt 2 | 0 | 0 | 0 | 2 |
| Quaternary ammonium salt 3 | 0 | 0 | 0 | 3 |
| Quaternary ammonium salt 4 | 0 | 0 | 0 | 2 |
| Quaternary ammonium salt 5 | 0 | 0 | 0 | 1 |

Skin irritation (II) of a quaternary ammonium salt

The brachial inside part of each of 15 healthy males was sealed for 48 hours with a fin chamber, to which a filter paper impregnated with about 0.02 ml (concentration: 0.3%) of a quaternary ammonium salt sample had been attached, being closed. Forty eight hours later, the fin chamber was removed and the condition of the skin after 3 hours, 24 hours, 48 hours was judged. The evaluation was conducted in accordance with the following standards and average grades of 15 males are shown in Table 5 as results.

| Standard for judgment | Grades |
| --- | --- |
| No reaction was recognized | 0 |
| A slight erythema was recognized | 1 |
| An apparent erythema was recognized | 2 |

TABLE 5

|  | Average grade | | |
| --- | --- | --- | --- |
|  | 3 hours | 24 hours | 48 hours |
| Quaternary ammonium salt 1 | 0.47 | 0.20 | 0.27 |
| Quaternary ammonium salt 2 | 0.40 | 0.20 | 0.13 |
| Quaternary ammonium salt 3 | 0.47 | 0.27 | 0.40 |
| Quaternary ammonium salt 4 | 0.33 | 0.13 | 0.20 |
| Quaternary ammonium salt 5 | 0.27 | 0.13 | 0.07 |

EXAMPLE 2

Tests on the sterilizing effects by washing and also by using were conducted using preparations obtained in accordance with Formulations 1–11 shown in Tables 6–16, respectively. The amounts in the Formulations are all expressed as parts by weight.

TABLE 6

Formulation 1: Detergent for fingers and hands

| Quaternary ammonium salt of the invention product or comparative product | 2.5 |
| --- | --- |
| Alkyl glucoside (effective content: 40%)*) | 40.0 |
| POE (20) sorbitan monolaurate ester | 1.0 |
| Sorbitol | 5.0 |
| Purified water | Balance |
|  | 100.0 |

*)alkyl ($C_{8-14}$, 10.4 on average) glucoside (polymerization degree n = 1.3)

TABLE 7

Formulation 2: Body Detergent

| Quaternary ammonium salt of the invention product or comparative product | 3.0 |
| --- | --- |
| Lauric acid | 15.0 |
| Lauroyl diethanol amide | 5.0 |
| Lauryldimethylamine oxide solution (35%) | 5.0 |
| Glycerin | 20.0 |
| Chelating agent | 1.2 |
| Potassium hydroxide | 4.2 |
| Purified water | Balance |
|  | 100.0 |

TABLE 8

Formulation 3: Shampoo

| Quaternary ammonium salt of the invention product or comparative product | 3.0 |
| --- | --- |
| Sodium POE (3) laurylether sulfate (30%) | 30.0 |
| Lauroyldiethanol amide | 9.0 |
| Glycerin | 5.0 |
| Chelating agent | 1.2 |
| Purified Water | Balance |
|  | 100.0 |

TABLE 9

Formulation 4: Rinse

| | |
|---|---|
| Quaternary ammonium salt of the invention product or comparative product | 3.0 |
| Silicone oil | 3.0 |
| Liquid paraffin | 1.0 |
| Cetyl alcohol | 1.5 |
| Stearyl alcohol | 1.0 |
| Stearyl trimethyl ammonium chloride | 0.7 |
| Glycerin | 3.0 |
| Purified Water | Balance |
| | 100.0 |

TABLE 10

Formulation: Face Wash

| | |
|---|---|
| Quaternary ammonium salt of the invention product or comparative product | 5.0 |
| Laurylphosphoric acid | 20.0 |
| Sodium hydroxide | 3.1 |
| Lauryldimethylamine oxide solution (35%) | 2.5 |
| Propylene glycol | 3.0 |
| Glycerin | 15.0 |
| Chelating agent | 1.2 |
| Purified Water | Balance |
| | 100.0 |

TABLE 11

Formulation 6: Lotion

| | |
|---|---|
| Quaternary ammonium salt of the invention product or comparative product | 2.0 |
| 1,3-butylene glycol | 6.0 |
| Glycerin | 4.0 |
| Oleyl alcohol | 0.1 |
| POE (20) sorbitan monolaurate | 0.5 |
| POE (15) lauryl ether | 0.5 |
| Ethanol | 10.0 |
| Purified Water | Balance |
| | 100.0 |

TABLE 12

Formulation 7: Milky Lotion

| | |
|---|---|
| Quaternary ammonium salt of the invention product or comparative product | 4.0 |
| Cetyl alcohol | 1.0 |
| Vaseline | 2.0 |
| Squalane | 6.0 |
| Dimethyl polysiloxane | 2.0 |
| 1,3-butylene glycol | 4.0 |
| Glycerin | 4.0 |
| Oleyl alcohol | 0.1 |
| POE (10) monooleate | 1.0 |
| Glycerol monostearate | 1.0 |
| Ethanol | 5.0 |
| Purified Water | Balance |
| | 100.0 |

TABLE 13

Formulation 8: Cream

| | |
|---|---|
| Quaternary ammonium salt of the invention product or comparative product | 4.0 |
| Stearyl alcohol | 6.0 |
| Stearic acid | 2.0 |
| Hydrogenated lanoline | 4.0 |
| Squalane | 9.0 |
| 2-Octyldodecanol | 10.0 |
| 1,3-Butylene glycol | 6.0 |
| Polyethylene glycol 1500 | 4.0 |
| POE (25) cetyl ether | 3.0 |
| Glycerol monostearate | 2.0 |
| Purified Water | Balance |
| | 100.0 |

TABLE 14

Formulation 9: Hand Cream

| | |
|---|---|
| Quaternary ammonium salt of the invention product or comparative product | 3.0 |
| Glycerin | 20.0 |
| Urea | 2.0 |
| POE (60) glycerol isostearate | 2.5 |
| Cetanol | 4.0 |
| Vaseline | 2.0 |
| Liquid paraffin | 10.0 |
| Purified Water | Balance |
| | 100.0 |

TABLE 15

Formulation Example 10: Deodorant lotion

| | |
|---|---|
| Quaternary ammonium salt of the invention product or comparative product | 3.0 |
| Ethanol | 15.0 |
| 1,3-Butylene glycol | 3.0 |
| POE (40) hydrogenated castor oil | 0.5 |
| Water-soluble thickener | 1.0 |
| Purified Water | Balance |
| | 100.0 |

TABLE 16

Formulation 11: Sanitizer

| | |
|---|---|
| Quaternary ammonium salt of the invention product or comparative product | 3.0 |
| Ethanol | 30.0 |
| POE (20) sorbitan monolaurate | 3.0 |
| POE (25) hydrogenated castor oil | 2.0 |
| Purified Water | Balance |
| | 100.0 |

TABLE 17

Formulation 12: Quick-dry rubbing-in type disinfectant for hands and fingers

| | |
|---|---|
| Quaternary ammonium salt of the invention product or comparative product | 0.5 |
| Ethanol | 80.0 |
| 2-Ethylhexyl triglyceride | 3.0 |
| Allantoin | 0.5 |
| Purified Water | Balance |
| | 100.0 |

Test for sterilization effects by washing

Detergents were prepared in accordance with Formulations 1 and 2. The palms of the hands were wetted lightly with water, followed by draining off the water. The palms of the hands were then lightly pressed against an SCDLP agar medium. On the palms of the hands, 1.5 ml of each of the detergents of Formulations 1 and 2 was placed. The hands were rubbed for one minute for foaming, followed by washing away with running water for 30 seconds. Water was drained off lightly from the hands and then the palms of the hands were lightly pressed against the SCDLP agar medium. Bacterial on the SCDLP agar media before and after washing were cultured at 28° C. for 48 hours. In each case, the number of the colonies formed was counted, which was designated as the viable count. An average of the results obtained at n=3 in each example are shown in Table 18. In the table, the former number in the column of "Formulation" indicates the formulation example and the latter the kind of a quaternary ammonium salt (this will apply hereinafter equally).

TABLE 18

|  | Formulation | Viable count before washing | Viable count after washing |
|---|---|---|---|
| Quaternary ammonium salt 1 | 1-1 | 450 | 1 |
|  | 2-1 | 563 | 2 |
| Quaternary ammonium salt 2 | 1-2 | 568 | 2 |
|  | 2-2 | 420 | 3 |
| Quaternary | 1-3 | 633 | 4 |

TABLE 18-continued

|  | Formulation | Viable count before washing | Viable count after washing |
|---|---|---|---|
| ammonium salt 3 | 2-3 | 526 | 2 |
| Quaternary ammonium salt 4 | 1-4 | 594 | 102 |
|  | 2-4 | 588 | 132 |
| Quaternary ammonium salt 5 | 1-5 | 430 | 240 |
|  | 2-5 | 890 | 420 |
| Blank (running water) | 1-B | 453 | 252 |
|  | 2-B | 393 | 256 |

Tests for sterilization and chapping

The face wash, lotion, milky lotion and cream according to Formulations 5–8 were prepared. Six females were asked to use the face wash, lotion, milky lotion and cream consecutively for 5 days (n=2 in each type). The sterilizing effects and chapping of the skin were measured and at the same time, their impression of feeling upon use were heard (A—good, B—average, C—bad). Sterilization test was conducted as follows: SCDLP agar media (7.07 $cm^2$) were pressed against the facial skin before first washing on the first day, and against the facial skin 1 hour and also 4 hours after the lotion or the milky lotion was applied, whereby bacteria were collected. After they were cultured at 28° C. for 48 hours, the number of the colonies so formed was counted and designated as the viable count. Results are shown in Table 19.

TABLE 19

| | Formulation | | | | Viable count before face wash | Viable count 1 hr after face wash | Viable count 4 hrs after face wash | Chapping |
|---|---|---|---|---|---|---|---|---|
| | Face wash | Lotion | Milky lotion | Cream | | | | |
| Quaternary ammonium salt 1 | 5-1 | 6-1 | 7-1 | 8-1 | 32 | 0 | 0 | A |
| Quaternary ammonium salt 2 | 5-2 | 6-2 | 7-2 | 8-2 | 39 | 1 | 1 | A |
| Quaternary ammonium salt 3 | 5-3 | 6-3 | 7-3 | 8-3 | 27 | 1 | 10 | B |
| Quaternary ammonium salt 4 | 5-4 | 6-4 | 7-4 | 8-4 | 22 | 5 | 12 | A |
| Quaternary ammonium salt 5 | 5-5 | 6-5 | 7-5 | 8-5 | 29 | 11 | 20 | A |
| Blank (without sterilizer) | 5-B | 6-B | 7-B | 8-B | 40 | 21 | 33 | A |

Test 1 for effects of use of shampoo and rinse

The shampoo and rinse were prepared in accordance with Formulations 3 and 4, respectively, and the effects of their use were tested.

Quaternary-ammonium-salt-free shampoo and rinse (blank) were used for 2 weeks everyday. Then the hair was not washed for a full day and the next day, the scalp was observed and rated as follows:

A—nothing abnormal was observed

B—itch and dandruff were slightly observed or

C—itch and dandruff were observed

The shampoo and the rinse according to Formulations 3 and 4, respectively were thereafter used for two weeks. Then similarly, the hair was not washed for a full day and the next day the scalp was observed and rated as above (n=1). Results are shown in Table 20.

TABLE 20

|  | Blank Formulation | | | | Germicidal Formulation | | | |
|---|---|---|---|---|---|---|---|---|
|  | Formulation | | Condition of head skin | | Formulation | | Condition of head skin | |
|  | Shampoo | Rinse | Itch | Dandruff | Shampoo | Rinse | Itch | Dandruff |
| Quaternary ammonium salt 1 | 3-B | 4-B | C | C | 3-1 | 4-1 | A | A |
| Quaternary ammonium salt 2 | 3-B | 4-B | C | C | 3-2 | 4-2 | A | A |
| Quaternary ammonium salt 3 | 3-B | 4-B | C | C | 3-3 | 4-3 | B | B |
| Quaternary ammonium salt 4 | 3-B | 4-B | C | C | 3-4 | 4-4 | C | C |
| Quaternary ammonium salt 5 | 3-B | 4-B | C | C | 3-5 | 4-5 | C | C |

Test 2 for effects of use of deodorant lotion

The deodorant lotion was prepared in accordance with Formulation 10 and its effects from use was tested.

A quaternary-ammonium-salt-free lotion (blank) was applied to the armpit everyday for 2 weeks and the smell of the armpit was observed and rated. Similarly, the deodorant lotion of Formulation 10 was used everyday for 2 weeks and the smell of the armpit was observed and rated (n=5).

Evaluation was made in accordance with the following standards:

| Standards for judgment | Evaluation |
|---|---|
| Having substantially no smell | 0 |
| Having a slight smell | 1 |
| Having a smell | 2 |
| Having an offensive smell | 3 |
| Having a strong offensive smell | 4 |

TABLE 21

|  | Blank Formulation | | Sterilizer Formulation | |
|---|---|---|---|---|
|  | Formulation | Grades | Formulation | Grades |
| Quaternary ammonium salt 1 | 10-B | 2.6 | 10-1 | 0.8 |
| Quaternary ammonium salt 2 | 10-B | 2.8 | 10-2 | 0.6 |
| Quaternary ammonium salt 3 | 10-B | 2.8 | 10-3 | 1.0 |
| Quaternary ammonium salt 4 | 10-B | 2.2 | 10-4 | 1.8 |
| Quaternary ammonium salt 5 | 10-B | 3.0 | 10-5 | 2.8 |

Tests for the effects of use of the sanitizer for bacterial removal

The sanitizer was prepared in accordance with Formulation 11 and its effects of use were tested.

5 ml of the sanitizer of Formulation 11 were added to a paper towel with which hands were then wiped. The palms of the hands before and after wiping were pressed against SCDLP agar media, whereby bacteria were collected. The bacteria so collected were cultured at 28° C. for 48 hours. The viable count after culturing was measured and a bacteria removal ratio was obtained in accordance with the following formula:

TABLE 22

$$\text{Bacteria removal ratio (\%)} = \frac{\text{(Viable count before treatment} - \text{viable count after treatment)}}{\text{Viable count before treatment}} \times 100$$

The average of each preparation (n = 3) is shown in Table 22

|  | Formulation | Bacteria removal rate (%) |
|---|---|---|
| Quaternary ammonium salt 1 | 11-1 | 98 |
| Quaternary ammonium salt 2 | 11-2 | 97 |
| Quaternary ammonium salt 3 | 11-3 | 98 |
| Quaternary ammonium salt 4 | 11-4 | 82 |
| Quaternary ammonium salt 5 | 11-5 | 56 |
| Blank (purified water) | 11-B | 32 |

Test 3 for the effects of use of the hand cream

The hand cream was prepared in accordance with Formulation 9 and its effects of use were tested.

After hands were washed with the detergent for hands and fingers of Formulation 1 (for which quaternary ammonium salt 1 was used), the hand cream of Formulation 9 was applied to the hands. After ordinarily spending one hour, the palms of the hands were pressed against an SCDLP agar medium, whereby bacteria were collected. The bacteria so collected were cultured at 28° C. for 48 hours. The number of the colonies after culturing was measured and designated as the viable count left. Average of the viable count of each preparation (n=2) is shown in Table 23.

TABLE 23

| Formulation | | Viable count before application of hand cream | Viable count after application of hand cream |
|---|---|---|---|
| Quaternary ammonium salt 1 | 9-1 | 2 | 2 |
| Quaternary ammonium salt 2 | 9-2 | 2 | 3 |
| Quaternary ammonium salt 3 | 9-3 | 1 | 2 |
| Quaternary ammonium salt 4 | 9-4 | 3 | 10 |
| Quaternary ammonium salt 5 | 9-5 | 3 | 25 |
| Blank | 9-B | 2 | 40 |

Tests for the effects of use of the disinfectant for sterilization and antimicrobial force The quick-dry rubbing-in type disinfectant for hands and fingers was prepared in accordance with Formulation 12 and its effects from use were tested.

On the hands, 3 ml of the disinfectant were applied. The hands were rubbed against each other to spread the disinfectant all over the hands and fingers uniformly. The palms of the hands were pressed against SCDLP agar media before and after the use of the disinfectant, respectively, to collect bacteria. The bacteria so collected were cultured at 28° C. for 48 hours.

Once after two hours and again after four hours after the treatment with the disinfectant, the palms of the hands were pressed against the SCDLP agar media, whereby bacteria were collected, respectively. The bacteria so collected were cultured at 28° C. for 48 hours.

The number of the colonies after culturing was measured and a sterilizing ratio and antimicrobial value were obtained in accordance with the following formulas:

$$\text{Sterilizing ratio (\%)} = \frac{(\text{Viable count before treatment} - \text{viable count just after treatment})}{\text{Viable count before treatment}} \times 100$$

$$\text{Antimicrobial value} = \frac{\text{Viable count with the passage of time}}{\text{Viable count just after the treatment}}$$

Standards of judgement:

A: Antimicrobial value less than 1
B: Antimicrobial value at least 1 but less than 2
C: Antimicrobial value at least 2 but less than 5
D: Antimicrobial value at least 5
The average of each preparation (n = 3) is shown in Table 24.

TABLE 24

| | Formulation | Sterilizing ratio (%) | Antimicrobial value after 2 hrs | Antimicrobial value after 4 hrs | Judgement after 4 hours |
|---|---|---|---|---|---|
| Quaternary ammonium salt 1 | 12-1 | 99.7 | 0.7 | 0.9 | A |
| Quaternary ammonium salt 2 | 12-2 | 99.0 | 0.57 | 0.76 | A |
| Quaternary ammonium salt 3 | 12-3 | 98.3 | 1.0 | 1.46 | B |
| Quaternary ammonium salt 4 | 12-4 | 92.0 | 1.03 | 1.33 | B |
| Quaternary ammonium salt 5 | 12-5 | 88.7 | 1.27 | 2.07 | C |
| Blank (purified water) | 12-B | 20.0 | 2.0 | 5.0 | D |

What is claimed is:

1. A germicidal composition comprising:
   i) a compound of formula (1):

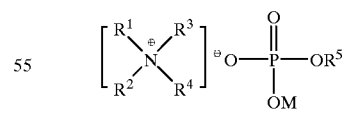

(1)

wherein at least one of $R^1$, $R^2$ and $R^3$ represents a linear or branched $C_{8-30}$ alkyl or alkenyl group and the remaining groups are the same of different and individually represent a methyl, ethyl or benzyl group; $R^4$ represents a methyl or ethyl group; $R^5$ represents a linear or branched $C_{1-30}$ alkyl or alkenyl group, or a polyoxyalkylene alkyl ether or polyoxyalkylene alkenyl ether having a linear or branched $C_{1-30}$ alkyl or alkenyl group; and M represents a hydrogen atom or an alkali metal atom; and ii) a compound of formula (2):

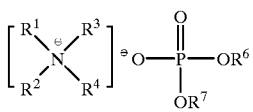

(2)

wherein $R^1$ to $R^4$ have the same meanings as defined above and $R^6$ and $R^7$ are the same or different and individually have the same meanings as $R^5$;
wherein the weight ratio of said compound (1) to said compound (2) is from 99:1 to 80:20.

2. The germicidal composition of claim 1, wherein $R^1$ is a linear $C_{8-20}$ alkyl group.

3. The germicidal composition of claim 1, wherein $R^1$ is a linear or branched $C_{8-20}$ alkyl or alkenyl group; $R^3$ is a benzyl group; $R^3$ is a methyl group; $R^5$, $R^6$ and $R^7$ are linear or branched $C_{12-20}$ alkyl groups; and M is a hydrogen atom.

4. The germicidal composition of claim 1, wherein $R^5$, $R^6$ and $R^7$ are the same or different and individually represent a linear or branched $C_{12-20}$ alkyl or alkenyl group.

5. The germicidal composition according to claim 1, wherein $R^1$ represents a linear or branched $C_{9-30}$ alkyl or alkenyl group; $R^2$ represents a benzyl group; and $R^3$ represents a methyl group.

6. The germicidal composition according to claim 1, wherein the compounds represented by the formulas (1) and (2) each has a chlorine ion content of less than or equal to 2.0%.

7. A germicidal composition comprising the product resulting from mixing:
i) a compound of formula (1):

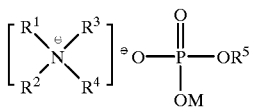

(1)

wherein at least one of $R^1$, $R^2$ and $R^3$ represents a linear or branched $C_{8-30}$ alkyl or alkenyl group and the remaining groups are the same or different and individually represent a methyl, ethyl or benzyl group; $R^4$ represents a methyl or ethyl group; $R^5$ represents a linear or branched $C_{1-30}$ alkyl or alkenyl group, or a polyoxyalkylene alkyl ether or polyoxyalkylene alkenyl ether having a linear or branched $C_{1-30}$ alkyl or alkenyl group; and M represents a hydrogen atom or an alkali metal atom; and
ii) a compound of formula (2):

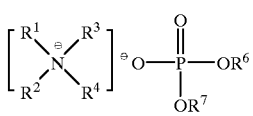

(2)

wherein $R^1$ to $R^4$ have the same meanings as defined above and $R^6$ and $R^7$ are the same or different and individually have the same meanings as $R^5$;
wherein the weight ratio of said compound (1) to said compound (2) is from 99:1 to 80:20.

8. The germicidal composition of claim 1, wherein the total concentration of said compound (1) and said compound (2) is within the range of 0.005 to 90 wt. % based on the total composition.

9. A germicidal detergent composition comprising:
(a) a composition comprising
i) a compound of formula (1):

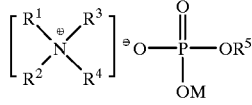

(1)

wherein at least one of $R^1$, $R^2$ and $R^3$ represents a linear or branched $C_{8-30}$ alkyl or alkenyl group and the remaining groups are the same or different and individually represent a methyl, ethyl or benzyl group; $R^4$ represents a methyl or ethyl group; $R^5$ represents a linear or branched $C_{1-30}$ alkyl or alkenyl group, or a polyoxyalkylene alkyl ether or polyoxyalkylene alkenyl ether having a linear or branched $C_{1-30}$ alkyl or alkenyl group; and M represents a hydrogen atom or an alkali metal atom; and
ii) a compound of formula (2):

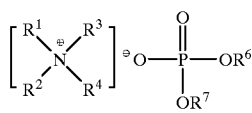

(2)

wherein $R^1$ to $R^4$ have the same meanings as defined above and $R^6$ and $R^7$ are the same or different and individually have the same meanings as $R^5$; and
(b) at least one surfactant selected from the group consisting of alkyl glycosides, sugar amides and a mixture thereof;
wherein the weight ratio of said compound (1) to said compound (2) is 99:1 to 80:20.

10. A germicidal detergent composition comprising the product resulting from mixing:
(a) a composition comprising
i) a compound of formula (1):

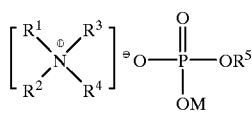

(1)

wherein at least one of $R^1$, $R^2$ and $R^3$ represents a linear or branched $C_{8-30}$ alkyl or alkenyl group and the remaining groups are the same or different and individually represent a methyl, ethyl or benzyl group; $R^4$ represents a methyl or ethyl group; $R^5$ represents a linear or branched $C_{1-30}$ alkyl or alkenyl group, or a polyoxyalkylene alkyl ether or polyoxyalkylene alkenyl ether having a linear or branched $C_{1-30}$ alkyl or alkenyl group; and M represents a hydrogen atom or an alkali metal atom; and
ii) a compound of formula (2):

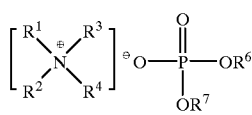

(2)

wherein $R^1$ to $R^4$ have the same meanings as defined above and $R^6$ and $R^7$ are the same or different and individually have the same meanings as $R^6$; and (b) at least one surfactant selected from the group consisting of alkyl glycosides, sugar amides and a mixture thereof;

wherein the weight ratio of said compound (1) to said compound (2) is 99:1 to 80:20.

11. The germicidal detergent composition of claim 9, wherein said alkyl glycoside has the following formula (3):

$$R^8\text{—}O\text{—}(R^9O)_m\text{—}(G)_n \qquad (3)$$

wherein $R^8$ represents a linear or branched $C_{8-18}$ alkyl, alkenyl or alkylphenyl group; $R^9$ represents a $C_{2-4}$ alkylene group, G represents a $C_{5-6}$ reducing sugar; m is an integer from 0–10; and n is an integer from 1–10 on average.

12. The germicidal detergent composition of claim 9, wherein said sugar amide has the following formula (4):

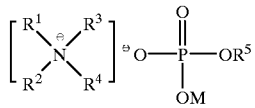

(4)

wherein $R^{10}$ represents a linear or branched $C_{5-31}$ alkyl or alkenyl group which may be substituted by a hydroxyl group; $R^{11}$ represents a hydrogen atom or a linear or branched $C_{1-4}$ alkyl group which may be substituted by a hydroxyl group; and Z represents a sugar residue or a sugar alcohol residue or an alkoxylated derivative of the residue.

13. A method for washing the skin or hair comprising applying the composition of claim 9.

14. A germicidal detergent composition comprising:
(a) a composition comprising
  i) a compound of formula (1):

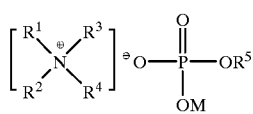

(1)

wherein at least one of $R^1$, $R^2$ and $R^3$ represents a linear or branched $C_{8-30}$ alkyl or alkenyl group and the remaining groups are the same or different and individually represent a methyl, ethyl or benzyl group; $R^4$ represents a methyl or ethyl group; $R^5$ represents a linear or branched $C_{1-30}$ alkyl or alkenyl group, or a polyoxyalkylene alkyl ether or polyoxyalkylene alkenyl ether having a linear or branched $C_{1-30}$ alkyl or alkenyl group; and M represents a hydrogen atom or an alkali metal atom; and
  ii) a compound of formula (2):

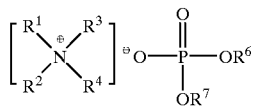

(2)

wherein $R^1$ to $R^4$ have the same meanings as defined above and $R^6$ and $R^7$ are the same or different and individually have the same meanings as $R^5$; and (c) at least one humectant selected from the group consisting of sorbitol, glycerin and a mixture thereof;

wherein the weight ratio of said compound (1) to said compound (2) is 99:1 to 80:20.

16. A method for washing the skin or hair comprising applying the composition of claim 15.

17. The composition according to claim 1, further comprising ethanol.

18. A method for sterilizing the skin comprising washing the skin with the composition of claim 1.

19. A method for sterilizing the skin comprising washing the skin with the composition of claim 18.

20. The germicidal detergent composition of claim 10, wherein said alkyl glycoside has the following formula (3):

$$R^8\text{—}O\text{—}(R^9O)_m\text{—}(G)_n \qquad (3)$$

wherein $R^8$ represents a linear or branched $C_{9-18}$ alkyl, alkenyl or alkylphenyl group; $R^9$ represents a $C_{2-4}$ alkylene group; G represents a $C_{5-6}$ reducing sugar; m is an integer from 0–10; and n is an integer from 1–10 on average.

21. The germicidal detergent composition of claim 10, wherein said sugar amide has the following formula (4):

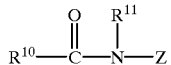

(4)

wherein $R^{10}$ represents a linear or branched $C_{5-31}$ alkyl or alkenyl group which may be substituted by a hydroxyl group; $R^{11}$ represents a hydrogen atom or a linear or branched $C_{1-4}$ alkyl group which may be substituted by a hydroxyl group; and Z represents a sugar residue or a sugar alcohol residue or an alkoxylated derivative of the residue.

22. A method for washing the skin or hair comprising applying the composition of claim 10.

15. A germicidal detergent composition comprising the product resulting from mixing:
(a) a composition comprising

* * * * *

UNITED STATES PATENT AND TRADEMARK OFFICE
CERTIFICATE OF CORRECTION

PATENT NO. : 6,008,177
DATED : December 28, 1999
INVENTOR(S) : Juri SATA et al.

It is certified that error appears in the above-identified patent and that said Letters Patent is hereby corrected as shown below:

On the title page, item [86], the PCT information is erroneously listed. It should be:

--PCT No.: PCT/JP96/03451

§ 371 Date: Jun. 8, 1998

§ 102(e) Date: Jun. 8, 1998--

Signed and Sealed this

Twenty-third Day of January, 2001

Attest:

Q. TODD DICKINSON

*Attesting Officer*  *Commissioner of Patents and Trademarks*